(12) United States Patent
Thiberg

(10) Patent No.: US 6,689,124 B1
(45) Date of Patent: Feb. 10, 2004

(54) DEVICE FOR CONTROLLING TREATMENT ADMINISTERED EXTERNALLY WITH THE AID OF LIGHT

(75) Inventor: Rolf Thiberg, Åkersberga (SE)

(73) Assignee: Biolight Patent Holding AB, Danderyd (SE)

( * ) Notice: Subject to any disclaimer, the term of this patent is extended or adjusted under 35 U.S.C. 154(b) by 0 days.

(21) Appl. No.: 09/889,213

(22) PCT Filed: Jan. 13, 2000

(86) PCT No.: PCT/SE00/00045
§ 371 (c)(1),
(2), (4) Date: Oct. 17, 2001

(87) PCT Pub. No.: WO00/44441

PCT Pub. Date: Aug. 3, 2000

(30) Foreign Application Priority Data

Jan. 13, 1999 (CH) .............................. 9900075

(51) Int. Cl.[7] .............................. A61B 18/18
(52) U.S. Cl. .............................. 606/9; 607/88
(58) Field of Search ............... 606/2, 9, 13, 11, 606/16

(56) References Cited

U.S. PATENT DOCUMENTS

| | | | |
|---|---|---|---|
| 5,259,380 A | * | 11/1993 | Mendes et al. ............. 607/115 |
| 5,562,717 A | * | 10/1996 | Tippey et al. ................. 607/41 |
| 5,616,140 A | * | 4/1997 | Prescott ........................ 606/10 |
| 5,800,479 A | * | 9/1998 | Thiberg ........................ 607/88 |
| 5,860,967 A | * | 1/1999 | Zavislan et al. ................ 606/9 |
| 6,063,108 A | * | 5/2000 | Salansky et al. .............. 607/89 |
| 6,126,651 A | * | 10/2000 | Mayer ............................ 606/1 |
| 6,221,095 B1 | * | 4/2001 | Van Zuylen et al. .......... 607/88 |

FOREIGN PATENT DOCUMENTS

| WO | WO 96/11723 | 4/1996 |
|---|---|---|
| WO | WO 97/46279 | 12/1997 |

* cited by examiner

*Primary Examiner*—Linda C. M. Dvorak
*Assistant Examiner*—Aaron Roane
(74) *Attorney, Agent, or Firm*—Alfred J. Mangels

(57) ABSTRACT

Apparatus for controlling external medical treatment administered with the aid of light, including a light-emitting device and a drive arrangement for driving the light-emitting device. The light-emitting device includes diodes that emit monochromatic light, and the light is pulsated in accordance with a predetermined series of pulse frequencies over predetermined time periods. The drive arrangement includes a computer and circuits for driving the light-emitting diodes, and the computer includes an input arrangement for inputting data relating to an intended treatment. The control apparatus includes a machine-readable card and an input device in the form of a card reader. The card is contains information relating to treatment programs, and the card reader delivers to the computer information read from the card.

9 Claims, 2 Drawing Sheets

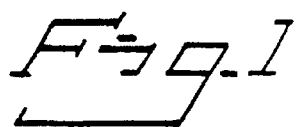
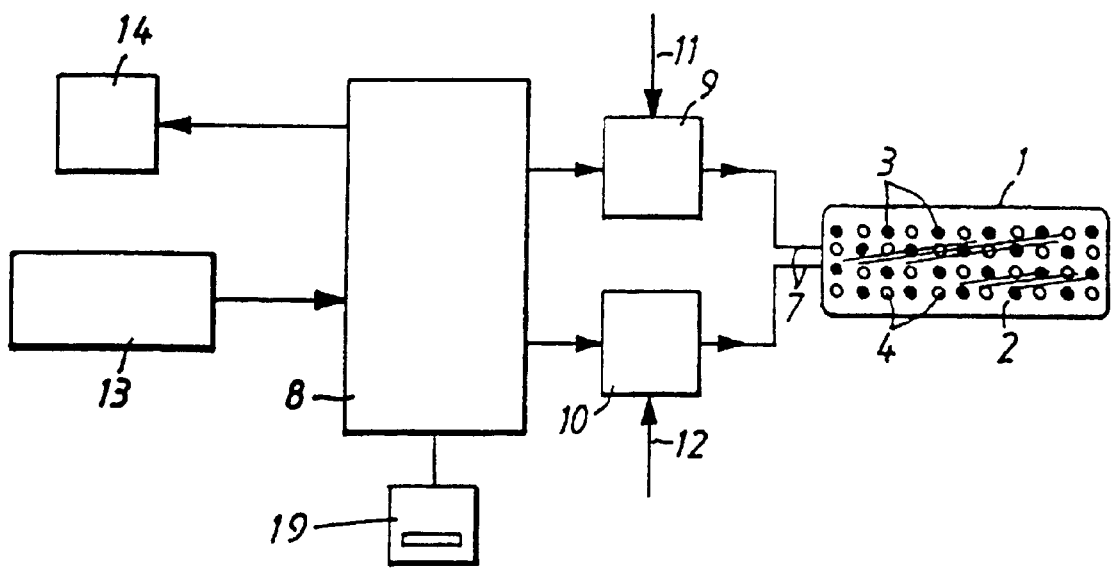
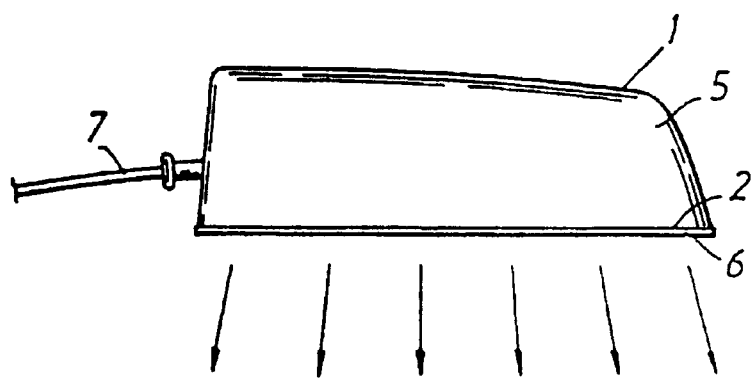

DEVICE FOR CONTROLLING TREATMENT ADMINISTERED EXTERNALLY WITH THE AID OF LIGHT

The present invention relates to a device for controlling external medical treatment with the aid of light, more specifically with light that palliates and/or cures different states of diseases.

Swedish Patent Specification No. 502 784 for example describes an apparatus for external medical treatment with the aid of light. The apparatus includes a light emitting device which is intended to be held against or in the close proximity of the patient's body, and drive means for operating the light emitting device. The light emitting device includes light emitting diodes or corresponding elements and is adapted to emit infrared light. According to the invention described in this patent specification, the means for driving the light emitting device is adapted to control said device to emit infrared light in a first stage and thereafter to emit visible light in a second stage. The drive means is also adapted to control the light emitting device to pulsate the infrared light and the visible light emitted, in accordance with a predetermined series of pulse frequencies.

It is also known to emit other types of monochromatic light for treating different states of diseases.

It is also known that a very good result can be achieved when treating solely with one or more types of monochromatic lights other than infrared light, such as with visible light of different colours, emitted according to a certain pulse frequency.

It has been found that an apparatus of the aforesaid kind can be used very successfully for treating many different types of diseases, wounds and injuries, for instance sport sustained injuries, stretched muscles, muscular pain, joint pain, headaches, various inflammatory conditions, various skin complaints, such as acne, back pains, etc., provided that the light is emitted in a certain way. In this regard, treatment with light has a favourable influence on injury healing processes and will palliate and/or cure various diseases.

There is thus an understanding that treatment with certain light that is emitted in certain frequency series will have a significantly greater effect in shortening the time taken to cure or palliate a disease.

According to said patent specification, data corresponding to the light treatment concerned is keyed into a computer through the medium of a computer keyboard.

According to another Swedish patent specification, viz Swedish Patent Specification No. 9900074-7, a greater or lesser part of the electronics required for energising the light-emitting diodes over certain time periods and at certain pulse repetition frequencies is provided in the light emitting device. According to one embodiment, all of the necessary electronics is mounted in the light emitting device.

Treatment of a complaint or injury is normally made by repeating a certain treatment a certain number of times, or the complaint/injury is subjected to a given number of successive treatments which differ from time to time.

In the known technology, it is thus necessary for the operator to keep an account of the treatments that shall be carried out and also an account of the order in which said treatments shall be performed and to set the apparatus correctly for a given treatment and to key-in the requisite data.

The present invention solves this problem.

The present invention thus relates to an apparatus for controlling external medical treatment administered with the aid of light, wherein the apparatus includes a light emitting device which is intended to be held against or in the close proximity of the patient's body, and drive means for operating the light emitting device, wherein said light emitting device includes light emitting diodes or corresponding elements that emit monochromatic light, wherein said drive means is adapted to control the light emitting device to emit one or more types of monochromatic light over one or more predetermined time periods and to pulsate the light emitted in accordance with a predetermined pulse frequency or series of pulse frequencies over said time periods, wherein said drive means includes a computer and diode drive circuits, wherein the computer includes an input means for the input of data relating to the treatment concerned, wherein the computer is adapted to deliver electric signals to the drive circuits and the intended light-emitting diodes are adapted to emit light within predetermined time periods and at predetermined pulse repetition frequencies, and wherein the control apparatus is characterised by a machine readable card and an input device in the form of a card reader; in that the machine readable card is adapted to contain information relating to one or more treatment programs; and in that the card reader is adapted to deliver information read from said card to said computer.

The invention will now be described in more detail partly with reference to an exemplifying embodiment thereof shown in the accompanying drawings, in which FIG. 1 is a schematic block diagram illustrating an apparatus of the aforesaid kind;

FIG. 2 is a side view of a light emitting device;

Figure 3:
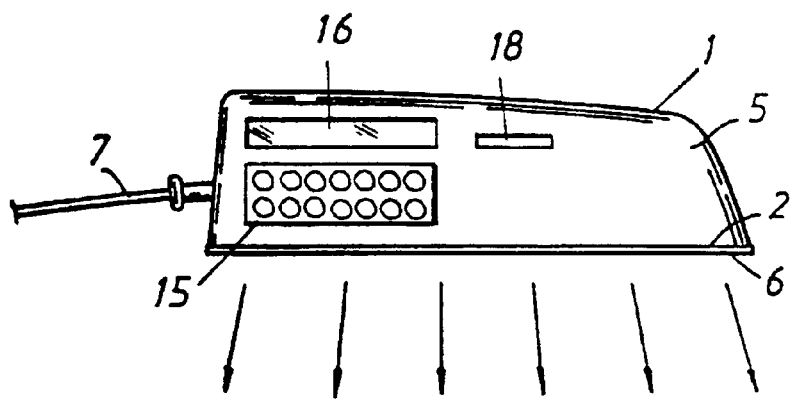
FIG. 3 illustrates a modified version of the inventive apparatus.
Figure 4:
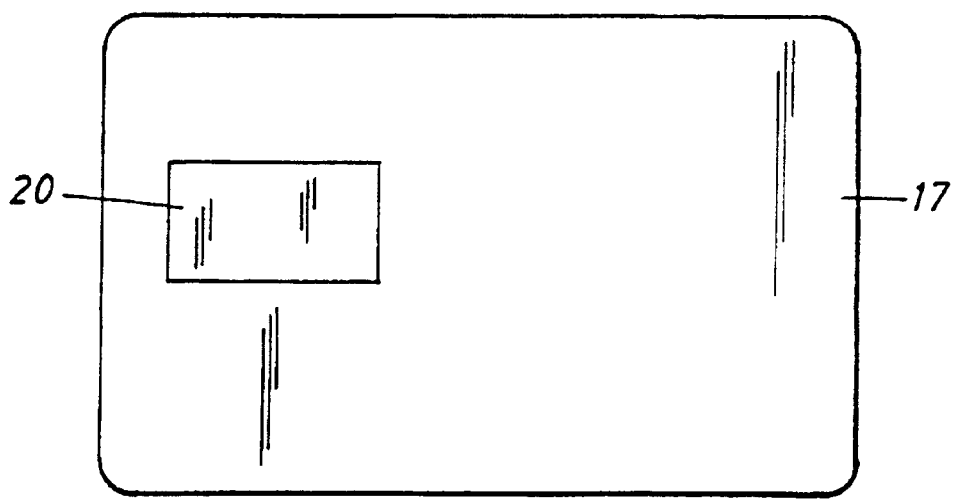
FIG. 4 illustrates a machine readable card.

FIGS. 1 and 2 illustrate generally an apparatus for external medical treatment with the aid of light, said apparatus including a light emitting device 1 which is intended to be held against or in the close proximity of the patient's body. The light emitting device is shown from one side in FIG. 2 and from beneath in FIG. 1. This device includes a casing 5 which houses a transparent plate 6. Located beneath the plate 6 is a surface 2 on which a plurality of light emitting diodes 3, 4 or corresponding elements are mounted.

The light emitting diodes emit light through the plate 6 when energised, i.e. when supplied with current through a cable 7.

When the device is being used, the casing 5 is held so that the plate 6 will lie against the relevant part of the patient's body.

The apparatus also includes drive means for the light emitting device 1. The drive means is designed to control the light emitting device 1 to emit different monochromatic light of different wavelengths over different predetermined time periods, and to pulsate the light emitted in accordance with a predetermined pulse frequency or series of pulse frequencies over said time periods.

The light-emitting device 1 includes light-emitting diodes 4 which are adapted to emit monochromatic visible light in one of the colors violet, blue, yellow, orange, red or green, and also infrared light and other invisible wavelengths.

The drive means includes a computer 8 which controls drive circuits 9, 10 to which signals for driving or operating the light emitting diodes are sent from the computer via the cable 7.

The computer and the drive circuits are of a suitable known kind. The drive means or computer has connected thereto a keyboard 13 by means of which the operator can key-in data for causing the drive means to activate the light emitting device in a desired manner. The device will conveniently also include a display 14 for displaying the settings entered through the keyboard. This display may be the computer screen.

The light emitting device 1 includes light emitting diodes 4 which are adapted to emit essentially monochromatic visible light in one of the colours violet, blue, yellow, orange, red or green, and also infrared light and other invisible wavelengths.

The nature of the light used will depend on the disease or the type of injury to be treated.

A great part of the above description of the drawings is also found in the aforementioned patent specification.

According to Swedish Patent Specification No. 9900074-7 at least the drive circuits 9, 10 of the drive means are mounted in the light-emitting device 1.

According to one embodiment of the invention disclosed in this last-mentioned patent specification, the computer 8 is integrated in the light-emitting device 1. In this embodiment, the computer 8 is conveniently a microprocessor with associated memory. The computer 8 is programmed to cause the light-emitting diodes to carry out different treatment programs, through the medium of the drive circuits 9, 10. The various treatments to be carried out can be entered into the computer through the medium of an input means provided in the light-emitting device. One preferred embodiment is to arrange a simple, known keypad 15 with associated display 16 on the light-emitting device 1, as shown in FIG. 3.

According to the present invention, the control apparatus includes a machine readable card 17 and an input device in the form of a card reader 18; 19 for the machine readable card. The machine readable card 17 is adapted to contain information relating to one or more treatment programs. By treatment program is meant a program that controls which light-emitting diodes 3, 4 shall be activated to emit light within predetermined time periods and at predetermined pulse repetition frequencies in respect of the treatment intended.

The card reader 18; 19 is also adapted to deliver to the computer 8 information that is read from the card.

The computer may be stand free from the light emitting device 1, as shown in FIG. 1, or may be integrated in the light emitting device, as described above.

The card may be any suitable machine readable card or corresponding data carrier. The card reader 18; 19 is a known card reader that is suitable for the type of card concerned. The card reader 19 may be free-standing and connected to the computer 8, as shown in FIG. 1, or may be integrated in the light emitting device 1, as shown in FIG. 3. The card reader 18 is illustrated in FIG. 3 solely in the form of a slot into which the machine readable card is inserted.

According to one highly preferred embodiment of the invention, the card 17 is a so-called smart card with associated memory and processor 20. In this case, the card reader 18; 19 is adapted to store information in the card memory 20.

According to another preferred embodiment of the invention, the card 17 includes information relating to two or more mutually identical or mutually dissimilar treatments that are to be carried out over mutually sequential time periods.

According to another preferred embodiment of the invention, the card 17 contains information relating to the number of treatments that are to be carried out, wherewith the computer 8 is adapted to input the number of treatments that have been carried out in a series of treatments, through the medium of the card reader 18; 19.

The information which a given card is intended to contain is fed into the card memory with the aid of known infeed devices suitable to this end.

When a certain series of treatment is to be carried out, an operator keys the relevant data into a computer into which a program covering different treatments has been installed. When the operator has decided upon the series of treatment to be carried out, the computer will feed relevant information into the card memory 20 through the medium of a known infeed device. The infeed of information can be effected via the card reader or by means of a separate device.

When commencing treatment, the operator places the card in the card reader which reads the card and feeds the information, or parts thereof, into the computer. The computer is then ready to activate the light-emitting diodes in the manner intended.

In the case of a series of treatments, which may be identical or different, information relating to which treatment in said treatment series shall be commenced can be inserted into the card from the computer in conjunction with reading said card. This means that the computer will be activated automatically to carry out the next treatment in said treatment series when the card is next read.

According to one embodiment, as many different cards can be produced as the number of possible treatments, wherewith the cards are used repeatedly by the operator, who chooses a card corresponding to the treatment desired.

According to another embodiment, one card is produced for the patient concerned and will include the intended treatment series. When treating the patient concerned, the patient's card is read and the correct treatment in said treatment series will be carried out. In this case, the patient can pay the cost of the treatment in conjunction with production of the card.

It will thus be evident that the present invention solves the aforementioned problem.

Although the invention has been described with reference to a number of embodiments thereof, it will be evident that modifications can be made with respect to structural details.

The present invention is therefore not restricted to the aforedescribed embodiments thereof, since modifications and variations can be made within the scope of the accompanying claims.

What is claimed is:

1. Apparatus for controlling external medical treatment administered with the aid of light, said apparatus comprising: a light-emitting device to be held against or in the close proximity of a patient's body, and drive means including drive circuits for driving the light-emitting device, the light-emitting device including light-emitting elements that emit monochromatic light, and wherein the drive means causes the light-emitting device to emit monochromatic light of at least one wavelength over predetermined time periods and to pulsate the emitted light in accordance with a predetermined pulse frequency or series of pulse frequencies over the predetermined time periods; a computer coupled with the drive means for driving the light-emitting elements, wherein the computer includes data transfer means including a card reader for transferring information for a series of treatments between the computer and a machine-readable smart card having a memory and a processor; wherein the machine-readable smart card contains information relating to one or more treatment series for delivery to the drive circuits in the form of electrical signals so that relevant ones of the light-emitting elements emit light over predetermined time periods and at predetermined pulse repetition frequencies; wherein the card reader transfers from the computer to the smart card the number of treatments and order of treatments of a series of treatments that have been carried out so that after termination of a treatment session a succeeding treatment session commences with a next treatment in the series of treatments; wherein the card reader delivers to the computer treatment information that is read from the smart card; and wherein the computer, the drive means and the data transfer means are carried by the light-emitting device.

2. Control apparatus according to claim 1, wherein the card includes information relating to a plurality of treatments that are to be carried out at mutually sequential time periods.

3. Control apparatus according to claim 2, wherein each of the treatments is identical.

4. Control apparatus according to claim 2, wherein each of the treatments is different.

5. Control apparatus according to claim 1, wherein the card contains information relating to the number of treatments that are to be carried out; and wherein the computer is adapted to input to the card through the card reader the number of treatments that have carried out from a series of treatments.

6. Control apparatus according to claim 1, wherein the light-emitting elements are light-emitting diodes.

7. Control Apparatus in accordance with claim 1, wherein the machine-readable smart card contains information for a series of treatments to be administered to a given individual.

8. Control apparatus in accordance with claim 1, wherein the housing is a rigid structure and the drive means are carried in the housing.

9. Control apparatus in accordance with claim 8, including a card-receiving slot provided in a wall of the housing for receiving a card containing information relating to a predetermined series of light treatments.

* * * * *